United States Patent
Kogure

(10) Patent No.: US 11,717,209 B2
(45) Date of Patent: Aug. 8, 2023

(54) ABNORMALITY DETERMINATION APPARATUS AND NON-TRANSITORY COMPUTER READABLE MEDIUM STORING PROGRAM USED FOR THE SAME

(71) Applicant: PARAMOUNT BED CO., LTD., Tokyo (JP)

(72) Inventor: Takamasa Kogure, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 147 days.

(21) Appl. No.: 16/197,916

(22) Filed: Nov. 21, 2018

(65) Prior Publication Data

US 2019/0159695 A1    May 30, 2019

(30) Foreign Application Priority Data

Nov. 30, 2017    (JP) .................................. 2017-231225

(51) Int. Cl.
*A61B 5/024*    (2006.01)
*A61B 5/11*    (2006.01)
(Continued)

(52) U.S. Cl.
CPC .............. *A61B 5/364* (2021.01); *A61B 5/0205* (2013.01); *A61B 5/352* (2021.01); *A61B 5/6892* (2013.01); *A61B 5/7221* (2013.01); *A61B 5/7275* (2013.01); *A61B 5/02405* (2013.01); *A61B 5/02438* (2013.01); *A61B 5/02455* (2013.01); *A61B 5/1102* (2013.01); *A61B 5/113* (2013.01);
(Continued)

(58) Field of Classification Search
CPC ......... A61B 5/02; A61B 5/0205; A61B 5/349; A61B 5/7221; A61B 5/4812; A61B 5/746
See application file for complete search history.

(56) References Cited

U.S. PATENT DOCUMENTS

2007/0195989 A1* 8/2007 Tsubata .............. A61B 5/02455
382/100
2011/0112442 A1* 5/2011 Meger .................. A61B 5/4818
600/595
(Continued)

FOREIGN PATENT DOCUMENTS

JP    2005-110920 A    4/2005
JP        5692097        4/2015
(Continued)

OTHER PUBLICATIONS

English translation of JP 2005-110920 published on Apr. 2005. (Year: 2005).*
(Continued)

*Primary Examiner* — Allen Porter
*Assistant Examiner* — Adreanne A. Arnold
(74) *Attorney, Agent, or Firm* — Wenderoth, Lind & Ponack, L.L.P.

(57) ABSTRACT

In general, according to one embodiment, one aspect of the apparatus comprising a sensor configured to acquire biological signals of a user, the biological signals including first signals and second signals, reliability of the first signals being relatively higher than reliability of the second signals, and a controller configured to activate an alarm, if a ratio of a time period of first signals to a time period of the biological signals is less than a first threshold.

21 Claims, 11 Drawing Sheets

(51) Int. Cl.
  *A61B 5/364* (2021.01)
  *A61B 5/00* (2006.01)
  *A61B 5/0205* (2006.01)
  *A61B 5/352* (2021.01)
  *A61B 5/113* (2006.01)
  *A61B 5/0245* (2006.01)
(52) U.S. Cl.
  CPC ........... *A61B 5/1118* (2013.01); *A61B 5/4809* (2013.01); *A61B 5/4812* (2013.01); *A61B 5/746* (2013.01)

(56) References Cited

U.S. PATENT DOCUMENTS

| | | | | |
|---|---|---|---|---|
| 2012/0296571 | A1* | 11/2012 | Shinoda | G16H 20/30 |
| | | | | 702/19 |
| 2013/0278429 | A1* | 10/2013 | Sakai | A61B 5/7225 |
| | | | | 340/635 |
| 2016/0317074 | A1* | 11/2016 | Kawai | G06Q 20/10 |
| 2017/0135593 | A1* | 5/2017 | Huang | A61B 5/02416 |
| 2018/0206798 | A1* | 7/2018 | Murai | A61B 5/145 |
| 2019/0117092 | A1* | 4/2019 | Yamashita | A61B 5/02 |

FOREIGN PATENT DOCUMENTS

| | | |
|---|---|---|
| JP | 2016-202346 A | 12/2016 |
| JP | 2017-42386 | 3/2017 |

OTHER PUBLICATIONS

Ashley et al., "Cardiology Explained", London, Remedica, 2004, Chapters Conquering the ECG (Year: 2004).*

* cited by examiner

FIG. 4

| DATE AND TIME | HEART RATE |
|---|---|
| ⋮ | ⋮ |
| 2017/11/16 02:30:00 | 6 0 |
| 2017/11/16 02:30:30 | 5 8 |
| 2017/11/16 02:31:00 | 7 0 |
| 2017/11/16 02:31:30 | — |
| 2017/11/16 02:32:00 | — |
| 2017/11/16 02:32:30 | 8 5 |
| 2017/11/16 02:33:00 | — |
| 2017/11/16 02:33:30 | 6 6 |
| 2017/11/16 02:34:00 | 6 8 |
| ⋮ | ⋮ |

FIG. 5

| THRESHOLD NAME | VALUE |
|---|---|
| CALCULATED RATIO CALCULATION TIME PERIOD | 5 HOURS |
| THRESHOLD OF CALCULATED HEART RATE RATIO | 80% |
| THRESHOLD OF UNCALCULATED HEART RATE RATIO | 20% |

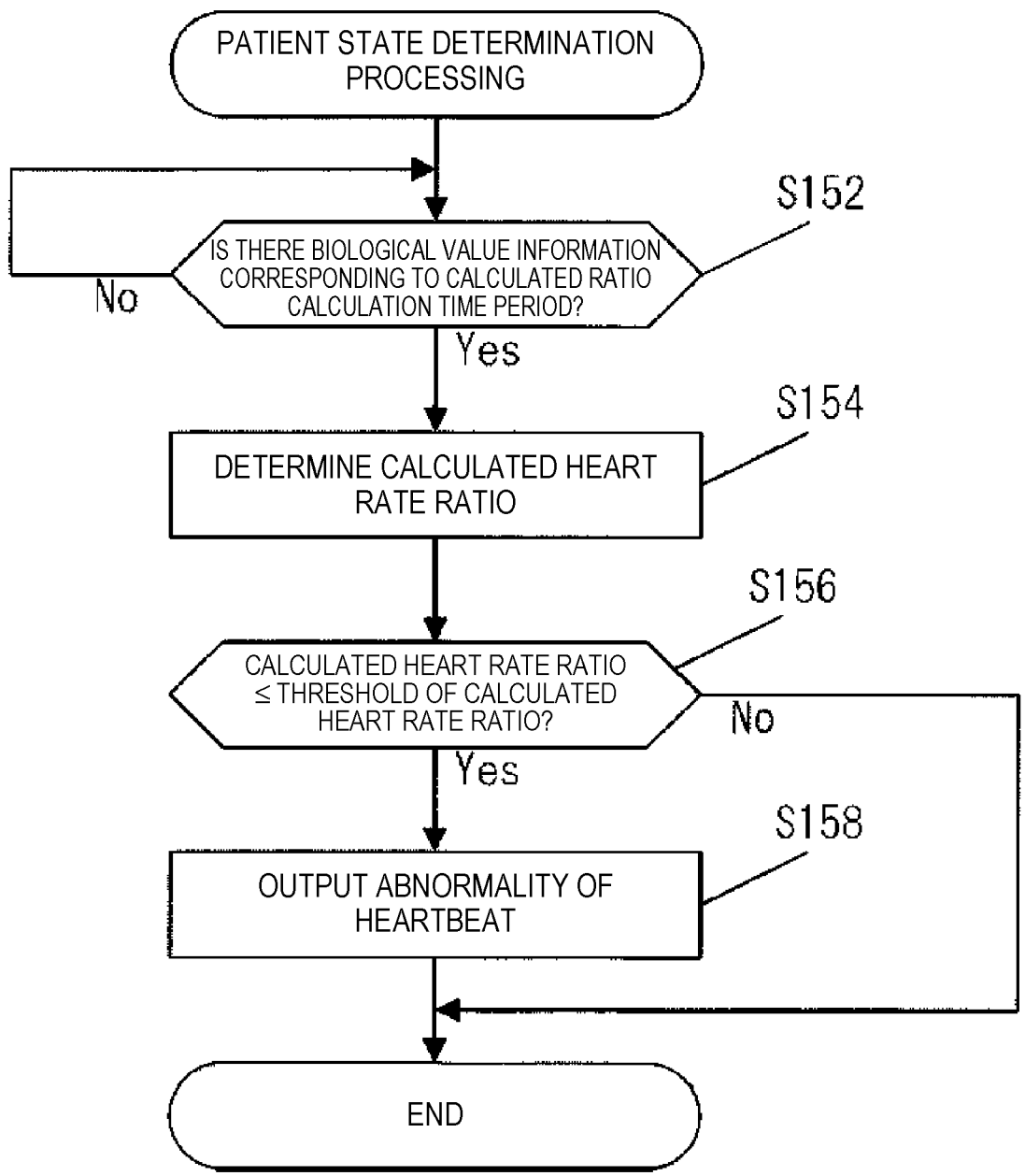

ABNORMALITY DETERMINATION APPARATUS AND NON-TRANSITORY COMPUTER READABLE MEDIUM STORING PROGRAM USED FOR THE SAME

CROSS-REFERENCE TO RELATED APPLICATIONS

This application is based upon and claims the benefit of priority from Japanese Patent Application No. 2017-231225, filed Nov. 30, 2017, the entire contents of which are incorporated herein by reference.

FIELD

The present embodiment relates to an abnormality determination apparatus and a non-transitory computer readable medium storing a program.

BACKGROUND

Conventionally, an apparatus which determines an abnormality in a heart rate and heartbeat rhythm of the patient has been known. The abnormality in the heart rate and the heartbeat rhythm can include, for example, arrhythmia. It is determined that there is an abnormality such as arrhythmia, for example, if an R-R interval from a peak point of an R wave to the next peak point of the R wave in an electrocardiogram is irregular.

BRIEF DESCRIPTION OF THE DRAWINGS

FIG. 4 is a diagram illustrating an example of a data table of biological information value data in the first embodiment;

FIG. 5 is a diagram illustrating an example of a parameter table in the first embodiment;

FIG. 8 is an operation flow for explaining patient state determination processing in the first embodiment;

DETAILED DESCRIPTION

Figure 1:
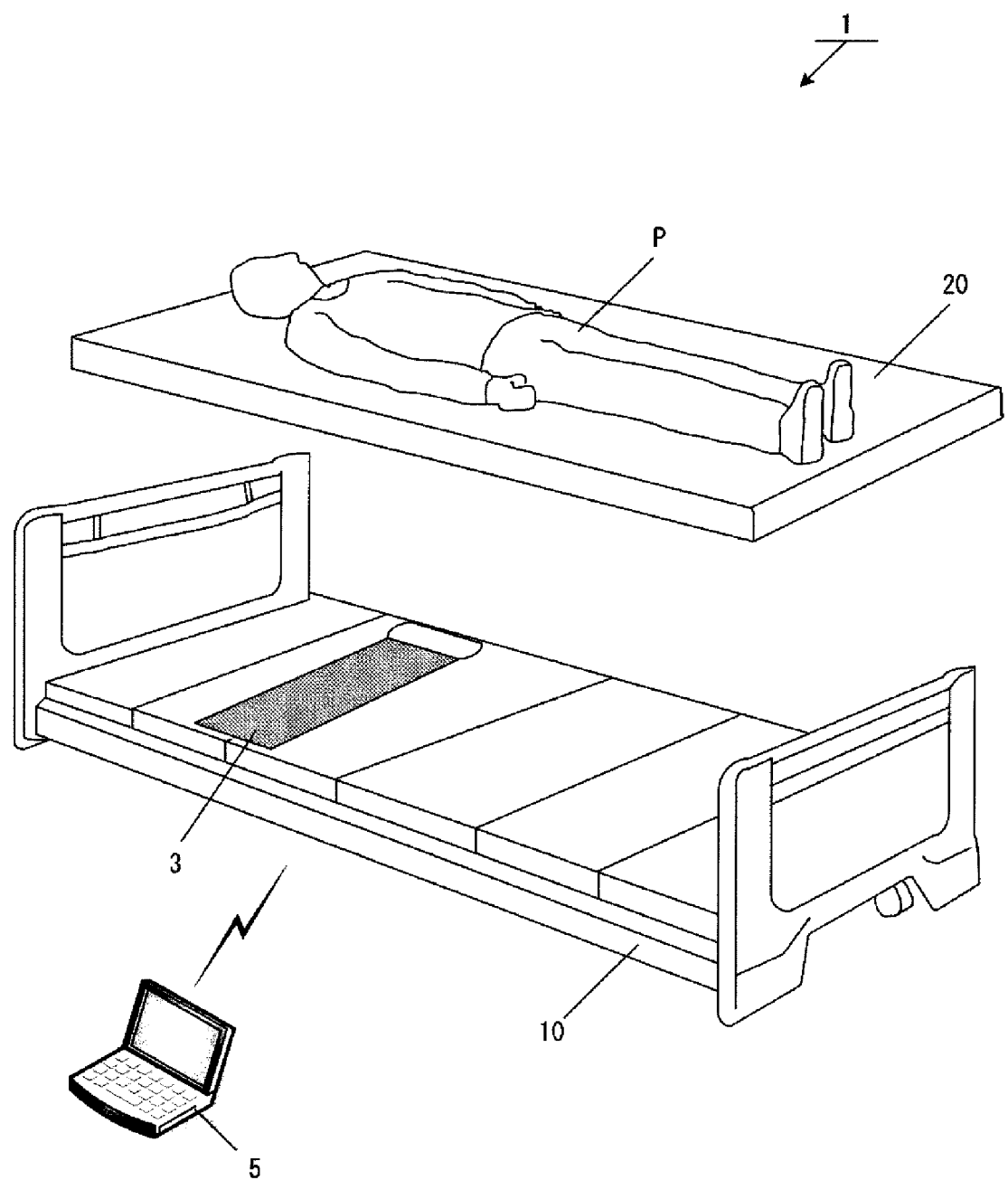
FIG. 1 is a diagram for explaining the whole configuration of a system in a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, according to one embodiment, one aspect of the apparatus comprising a sensor configured to acquire biological signals of a user, the biological signals including first signals and second signals, reliability of the first signals being relatively higher than reliability of the second signals, and a controller configured to activate an alarm, if a ratio of a time period of first signals to a time period of the biological signals is less than a first threshold.

In preferred embodiments, the biological signals may be a heart rate, and the controller may determine that there is an abnormality in a cardiopulmonary function of the user if the ratio is equal to or less than the first threshold.

In preferred embodiments, the controller may calculate a biological information of the user based on the biological signals if the user is lying down on a bed.

In preferred embodiments, the controller may determine a state of the user and calculates, as a calculated ratio, a ratio of the first signals if the user is sleeping.

In preferred embodiments, the controller may set one night as the time period of biological signals.

In preferred embodiments, the controller may set at least two or more days as the time period of biological signals.

another aspect of the method comprising acquiring, with a sensor, biological signals of a user, the biological signals including first signals and second signals, reliability of the first signals being relatively higher than reliability of the second signals, and activating, with a controller, an alarm, if a ratio of a time period of first signals to a time period of the biological signals is less than a first threshold.

In preferred embodiments, the biological signals may be a heart rate, the method further may be comprising determining, with the controller, that there is an abnormality in a cardiopulmonary function of the user if the ratio is equal to or less than the first threshold.

In preferred embodiments, the method further may be comprising calculating, with the controller, a biological information of the user based on the biological signals if the user is lying down on a bed.

In preferred embodiments, the method further may be comprising determining, with the controller, a state of the user and calculates, as a calculated ratio, a ratio of the first signals if the user is sleeping.

In preferred embodiments, the method further may be comprising setting, with the controller, one night as the time period of biological signals.

In preferred embodiments, the method further may be comprising setting, with the controller, at least two or more days as the time period of biological signals.

another aspect of the non-transitory computer readable medium having stored thereon a program for causing a computer to execute at least the following, acquiring biological signals of a user, the biological signals including first signals and second signals, reliability of the first signals being relatively higher than reliability of the second signals, and activating an alarm, if a ratio of a time period of first signals to a time period of the biological signals is less than a first threshold.

In preferred embodiments, the biological signals may be a heart rate, the program further may be causing a computer to execute at least the following, determining that there is an abnormality in a cardiopulmonary function of the user if the ratio is equal to or less than the first threshold.

In preferred embodiments, the program further may be causing a computer to execute at least the following, calculating a biological information of the user based on the biological signals if the user is lying down on a bed.

In preferred embodiments, the program further may be causing a computer to execute at least the following, determining a state of the user and calculates, as a calculated ratio, a ratio of the first signals if the user is sleeping.

In preferred embodiments, the program further may be causing a computer to execute at least the following, setting one night as the time period of biological signals.

In preferred embodiments, the program further may be causing a computer to execute at least the following, setting at least two or more days as the time period of biological signals.

Embodiments will be described below with reference to the drawings. In a comparison example, an abnormality of a biological signal such as arrhythmia is detected from irregularity of an R-R interval by utilizing an electrocardiograph. However, since it is difficult to accurately detect an R-R interval with a non-wearable type body motion sensor which measures respiratory movement and ballistocardiogram, it is difficult to determine an abnormality of biological information, such as arrhythmia by using the non-wearable type body motion sensor. When the non-wearable type body motion sensor (non-wearable sensor) is used, the non-wearable sensor usually doesn't contact user's body.

Figure 3:
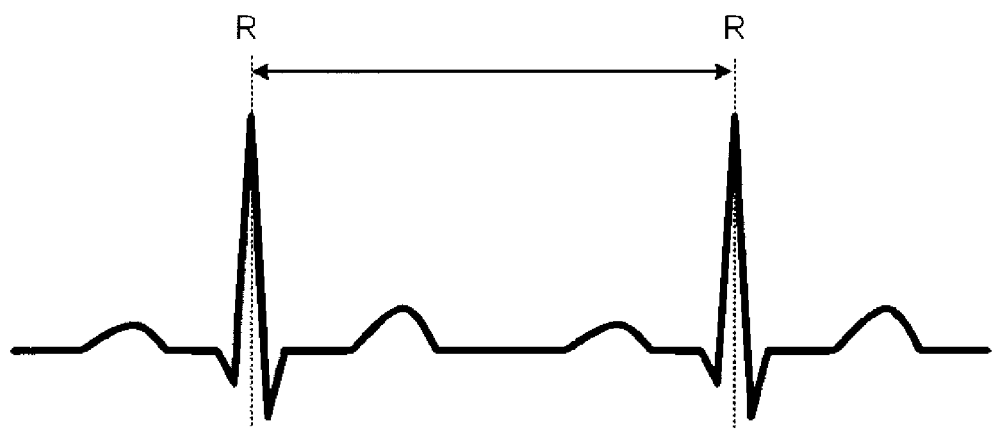
FIG. 3 is a diagram for explaining an R-R interval.

Note that, as an example of a method in the comparison example, an electrocardiogram is acquired with electrodes worn on a patient. FIG. 3 illustrates part of a waveform of the electrocardiogram. Here, for example, irregularity of the R-R interval of the electrocardiogram is determined. Then, if the R-R interval is irregular, arrhythmia is determined.

However, it is necessary for the user to wear electrodes, or to contact the electrodes on a user to acquire an electrocardiogram using an electrocardiograph. Further, if the electrodes move as a result of the user moving or noise such as myoelectric potential is mixed with a correct waveform, a correct waveform cannot be acquired. In particular, since an opportunity of acquiring an electrocardiogram using an electrocardiograph is limited, there is a trouble and problem that an abnormality such as arrhythmia can't be recognized or noticed sooner. For example, a normal healthy person has an opportunity of being examined with an electrocardiogram in a periodic health examination of once a year. The normal healthy person can't notice and recognize whether he or she has any trouble and abnormality related to the arrhythmia until executing the periodic health examination.

Therefore, the abnormality determination apparatus, or the like, described below makes it possible to easily determine an abnormality of biological information by utilizing a calculated data ratio of the acquired biological information. Further, since the non-wearable sensor isn't placed and contacted on the user, that is, the user doesn't care about using the non-wearable sensor at all, it becomes possible to acquire stable biological information during sleeping for a long period, so that it becomes possible to lower a possibility that an abnormality of biological information is missed.

[1. First Embodiment]
[1.1. Whole System]

FIG. 1 shows the whole system 1 of the abnormality determination apparatus according to a first embodiment is applied. As illustrated in FIG. 1, the system 1 includes a detection apparatus 3 placed between sections of the bed 10 and a mattress 20, and a processing apparatus 5 for processing a value output from the detection apparatus 3. The detection apparatus 3 and the processing apparatus 5 function as the abnormality determination system (abnormality determination apparatus). The bed 10 includes a base frame which is placed on a floor, a support frame which the base frame supports, a plurality of sections which the support frame supports, and at least one of drivers to drive the support frame and the sections. The sections include a back section, an upper leg section, a lower leg section, and a head section. Each section can move in accordance with the driver. The mattress 20 is placed on the sections.

If a user (hereinafter, referred to as a "patient P" as an example) lies down on the mattress 20, the detection apparatus 3 detects body vibration (vibration produced from a human body) as a biological signal of the patient P. Then, the processing apparatus calculates a biological information value of the patient P on the basis of the detected vibration. In the present embodiment, the calculated biological information value (at least a respiration rate, a heart rate and an amount of activity) is displayed on the processing apparatus 5 as the biological information value of the patient P. However, a storage unit, a display unit, and processor, or the like, can be provided on the detection apparatus 3, such that the system may be integrally formed. Further, because the processing apparatus 5 may be a general-purpose processing apparatus, the processing apparatus 5 is not limited to an information processing apparatus such as a computer and may be configured with an apparatus such as, for example, a tablet or a smartphone.

Further, the user may be an ailing person or a person who needs care. Further, the user may be a healthy person who does not need care, an elderly person, a child, a disabled person or an animal which is not a person.

Here, the detection apparatus 3 has a sheet shape so as to be thin. Therefore, even if the detection apparatus 3 is placed between the bed 10 (the sections of the bed) and the mattress 20, since the detection apparatus 3 can be used without providing a feeling of strangeness to the patient P, it is possible to measure a biological information value in bed for a long period. That is, a biological information value is acquired as a state of the patient when the user is lying on the bed, is in a resting state, or is at rest.

Note that the detection apparatus 3 only has to be able to acquire a biological signal (such as body motion, respiratory movement and ballistocardiogram) of the patient P. The processing apparatus calculates a heart rate and a respiration rate on the basis of body vibration. Alternatively, the detection apparatus 3 can be configured to include a microwave radar or laser speckle sensor to acquire the biological signal or to calculate a heart rate and a respiration rate on the basis of motion of a body surface detected by the microwave radar or the laser speckle sensor. The detection apparatus 3 can include a video camera, or an actuator with a strain gauge to acquire a biological signal of the patient. Further, the detection apparatus 3 may be implemented by, for example, a smartphone placed on the bed 10 with use of a built-in acceleration sensor, or a tablet placed on the bed 10 with use of a built-in acceleration sensor, or the like.

[1.2. Configuration of the System]

A configuration of the system 1 will be described using FIG. 2. The system 1 in the present embodiment includes the detection apparatus 3 and the processing apparatus 5. Although the system 1 includes a plurality of units in FIG. 2, all unit (processing) other than the biological signal acquiring unit 110 may be implemented by either one of the apparatuses. That is, the units including inputs such as detected or sensed information, outputs, and processing, described herein are implemented in hardware, such as detectors, sensors, microprocessors, input/output devices, displays, speakers, and software stored on electronic non-transitory memory, and such hardware can be physically included in either the processing device 5 or the sensor 3, or distributed between the processing device 5 or the sensor 3.

The system 1 (abnormality determination apparatus) includes a control unit 100, a biological signal acquiring unit 110, a biological information value calculating unit 120, a reliability evaluating unit 125, a sleep state determining unit 130, a patient state determining unit 140, a storage unit 150, an input unit 160 and an output unit 170.

The abnormality determination system 1 performs alerting (notification) operation after determining that a state of the patient is an abnormal state. If the system 1 determines the state of the patient is an abnormal state, a processing apparatus sends or activates an alert via an alert output unit 800, in a manner that can be noticed by caregivers like a staff or a family. The output unit 800 can be configured to include a sound generator and speaker to outputs or activates the alert (notification) or can issue or activates the alert on a screen display or may output or activates the alert as an electronic indication to a mobile terminal apparatus or other terminal apparatuses, or the like, through an e-mail, or the like.

The control unit 100 controls entire operations of the system 1 (abnormality determination apparatus). The control unit 100 is configured with, for example, a control apparatus such as a CPU (Central Processing Unit), microprocessor, etc. The control unit 100 performs processing by reading out and executing programs stored in the storage unit (electronic memory) 150. Note that, while, in the present embodiment, the control unit 100 operates for the whole system, the control unit 100 may be respectively provided at the detection apparatus 3 and the processing apparatus 5. In other words, the control unit can be implemented for the whole system by a microprocessor in either the processing apparatus 5 or the detection apparatus 3, or the control unit can be implemented by separate microprocessors handling respective functions in the processing apparatus 5 and the detection apparatus 3.

The biological signal acquiring unit 110 acquires a biological signal of the patient P. The biological signal acquiring unit 110 can include a pressure change sensor that detects body vibration which is one type of the biological signal. The biological information value calculating unit 120 converts the acquired body vibration into biological information value data such as a respiration rate, a heart rate and an amount of activity and outputs the biological information value data. Further, the biological information value calculating unit 120 can determine a state of the patient (for example, whether or not the patient P is lying down in the bed, whether the patient P gets out of the bed, postures the patient is staying in the bed, positions the patient is staying in the bed, or the like) on the basis of body vibration data or determine a state of the patient (whether the patient is sleeping or awaken) as will be described later.

Note that, while the biological signal acquiring unit 110 in the present embodiment, for example, acquires body vibration of the patient with a pressure sensor and acquires respiration and heartbeat from the body vibration, the biological signal acquiring unit 110 may acquire a biological signal from change in a position of the center of gravity (body motion) of the patient with a load sensor, may acquire a biological signal on the basis of motion of a body surface or bedclothes with a radar or may acquire a biological signal on the basis of sound picked up with a microphone by the microphone being provided. It is only necessary that a biological signal of the patient can be acquired using one of the sensors.

That is, the biological signal acquiring unit 110 may be provided in an apparatus such as the detection apparatus 3 or may be configured to receive a biological signal from external sensor apparatuses.

The biological information value calculating unit 120 calculates a biological information value (such as a respiration rate and a heart rate) of the patient P. In the present embodiment, it is also possible to extract a respiratory component and a heartbeat component from the body motion acquired by the biological signal acquiring unit 110 and obtain a respiration rate and a heart rate on the basis of a respiratory interval and an R-R interval. Further, it is also possible to analyze (perform Fourier transform, or the like, on) periodicity of the body motion and calculate a respiration rate and a heart rate from a peak frequency.

The reliability evaluating unit 125 determines whether or not reliability of the biological information value output from the biological information value calculating unit 120 is relatively high. Here, as evaluation as to whether the reliability of the biological information value is relatively high or low, a reliability evaluation method disclosed in Japanese Patent Laid-Open No. 2017-47211 (filing date: Sep. 1, 2016, title of the invention: BIOLOGICAL INFORMATION OUTPUT DEVICE, BIOLOGICAL INFORMATION OUTPUT METHOD, AND PROGRAM) can be incorporated. While the entire content of this patent application is incorporated by reference, one of the following methods is utilized as a specific method.

(1) Reliability Evaluation Using Calculation Conditions

The reliability evaluating unit 125 evaluates reliability of the biological information value on the basis of conditions of the patient in the case where the biological information value calculating unit 120 detects the biological information value or the biological information is calculated. For example, based on signals from sensors as discussed above, in the case where the patient is not in a lying state, that is, the patient is out of bed, or when the patient is in a seated position, since the biological information value is not accurate, the reliability evaluating unit 125 determines that the reliability is relatively low. Further, in the case where the system is externally connected to equipment such as a bedsore prevention air mattress, and when the external equipment causes vibration, since the biological information value is not accurate, the reliability evaluating unit 125 determines that the reliability is relatively low. At this time, the reliability evaluating unit 125 may utilize the patient state determining unit 140 to evaluate reliability of the biological information value.

(2) Reliability Evaluation in Biological Information Calculation Process

The reliability evaluating unit 125 evaluates the reliability of the biological information value on the basis of the process of calculating biological information. For example, the reliability evaluating unit 125 determines a variation (such as standard deviation and a variation coefficient) of exhalation/inhalation and an inter-beat interval, and when it is determined to be sufficiently large (that is, if the variation of a period between the exhalation and the inhalation is sufficiently large, if the variation of a period between the exhalation and an adjacent exhalation is sufficiently large, if the variation of a period between the inhalation and adjacent inhalation is sufficiently large, or if the inter-beat interval sufficiently large), the reliability evaluating unit 125 determines that the reliability is relatively low.

Further, the reliability evaluating unit 125 evaluates the reliability of the biological information value on the basis of an amplitude and variation of waveforms after filtering, and if there is variation in the amplitude, the reliability evaluating unit 125 determines that the reliability is relatively low.

For example, normally, an R-R interval (respiratory interval) within a short period of time becomes substantially equal. Therefore, in the case where there is irregularly large variation in the R-R interval (respiratory interval), since noise which is different from the biological information value on the patient is large, the reliability evaluating unit 125 determines that detection is not yet performed or erroneous detection is performed, and the reliability evaluating unit 125 determines that the reliability is relatively low.

Further, in the case where a plurality of sensors are provided, the reliability evaluating unit 125 evaluates the reliability of the biological information value on the basis of a difference in values calculated from the plurality of sensors. That is, in the case where the reliability evaluating unit 125 determines that a difference of the biological information values the plurality of sensors is sufficiently large, the reliability evaluating unit 125 determines that the reliability is relatively low.

Further, the biological information value calculating unit 120 can calculate the biological information value by analyzing periodicity of body motion data, and the reliability evaluating unit 125 evaluates the reliability of the biological information value from a degree of prominence of a peak of a frequency spectrum or variation in detection values of the plurality of sensors.

(3) Reliability Evaluation of Calculated Respiration Rate and Heart Rate

The reliability evaluating unit 125 determines that the reliability is relatively low in the case where the calculated heart rate and respiration rate largely deviate or are different from values calculated previously. For example, the case includes a case where a value more than double the value calculated for the heart rate before is calculated, a case where the respiration rate fluctuates by equal to or greater than a threshold, or the like.

Further, the reliability evaluating unit 125 may evaluate the reliability of the biological information value by calculating an average of values of past several times (for example, five pieces of the calculated biological information) and determine that reliability is relatively low in the case where a calculated value largely deviates from the average value or a tilt (differential value) is precipitous. Further, the reliability evaluating unit 125 may evaluate the reliability of the biological information value with a plurality of levels and may be output in a stepwise manner. For example, the reliability of the biological information value includes a relatively high, a relatively low. The reliability of the relatively low includes an extremely low, a slightly low. The reliability evaluating unit 125 can determine that the reliability is extremely low in the case where the biological information becomes more than double (or equal to or less than half) the biological information calculated in previous time and determine that the reliability is slightly low in the case where the biological information becomes equal to or more than 1.5 times and less than double (or equal to or more than half and less than two-thirds) the biological information calculated in previous time.

In the case where the calculated heart rate and respiration rate exceed predetermined thresholds or less than the thresholds, the reliability evaluating unit 125 determines that the reliability is relatively low. For example, in the case where the respiration rate is 0 or 1, in the case where the heart rate exceeds 200, or the like, the reliability evaluating unit 125 determines that the reliability is relatively low. Note that the thresholds may be set by a caregivers or doctor e.t.c, or may be set in accordance with age or a health condition of the patient.

The sleep state determining unit 130 determines a state of the patient. For example, the state of the patient is determined on the basis of the biological signal acquired by the biological signal acquiring unit 110. As the state of the patient, the state of the patient may include "waking" (the state the patient is waking) or "sleeping" (the state the patient is sleeping), or further, may include "REM sleep" (the state the patient is sleeping and a level of sleeping is REM) or "non-REM sleep" (the state the patient is sleeping and a level of sleeping is non-REM), or may include a depth level of sleeping.

The patient state determining unit 140 determines the state of the patient on the basis of the above-described biological signal and biological information value. In the present embodiment, an abnormality of a heart rate or a heartbeat rhythm of the patient is determined, and whether an abnormality in the biological information (for example, heartbeat) is determined. Note that, in the present embodiment, the patient state determining unit 140 detects arrhythmia of the patient on the basis of the heart rate as the biological information value and determines the state of the patient based thereon.

The storage unit 150 stores various kinds of data and programs for operation of the system 1. The control unit 100 implements various kinds of functions by reading out and executing the programs stored in the storage unit 150. The storage unit 150 is, for example, configured with a semiconductor memory, a magnetic disk apparatus, or the like.

In the storage unit 150, biological information value data 152, state data 154 and a parameter table 156 are stored.

In the biological information value data 152, the biological information value output from the biological information value calculating unit 120 is mainly stored. FIG. 4 is a diagram explaining an example of a data table of the biological information value data 152. In the biological information value data 152, the heart rate (for example, "58") is stored as the biological information value for each date and time (for example, "2017/11/16 02:30:30") on which the biological information value is calculated. Note that it is only necessary that the biological information value for each predetermined time period is periodically stored in the biological information value data 152. Therefore, only the biological information value (heart rate) may be periodically stored for each predetermined time period.

Further, a timing at which the biological information value is stored for each predetermined time period may be a timing at which the biological information value is stored in the biological information value data 152. A time period which becomes a criterion for calculating the biological information value may be 60 seconds before calculation. That is, a time period in which the biological information value is calculated may be different from a time period in which the biological information value is stored (output).

Note that, while, in the present embodiment, the heart rate is stored as the biological information value in the biological information value data 152, other biological information values such as the respiration rate may be stored in the biological information value data 152.

In the state data 154, the state of the patient is stored. As the state of the patient determined by the sleep state determining unit 130, "sleeping" or "waking" is stored. At this time, quality (depth level) of sleeping may be stored, or a state whether the patient is staying "in bed", or whether the patient gets out of the bed may be stored. The control unit 100 (patient state determining unit 140) can acquire a sleeping period of one night of the patient by referring to the state data 154.

In the parameter table 156, parameters to be utilized in the present embodiment are stored. As illustrated in FIG. 5, a plurality of parameters or thresholds are stored in the parameter table 156. In the parameter table 156, a calculated ratio calculation time period (for example, "5 hours") is stored. Further, in the parameter table 156, a threshold of calculated heart rate ratio (for example, "80%") and/or a threshold of uncalculated heart rate ratio (for example, "20%") is stored.

While content of the parameters will be described later, regarding to the calculated ratio calculation time period, the calculated ratio calculation time period is a necessary time period for determining the calculated heart rate ratio (the uncalculated heart rate ratio). Further, the threshold of calculated heart rate ratio is a threshold for determining that the heart rate is appropriately calculated within the calculated ratio calculation time period. The threshold of uncalculated heart rate ratio is a threshold for determining that the heart rate is not appropriately calculated within the calculated ratio calculation time period. In the case where a sum of the calculated and uncalculated ratios becomes 100%, it is only necessary to store one of the ratios in the parameter table 156. Further, in the case where different criteria are utilized, the ratios may be respectively stored in the parameter table 156.

The input unit 160 is utilized when caregivers or doctors input various conditions or inputs operation for starting measurement. For example, the input unit 160 is implemented by any input means such as a hardware key and a software key.

The output unit 170 is utilized when the biological information value such as the state of the patient ("sleeping", "waking", or the like), the heart rate and the respiration rate is output, or when a notification of an abnormality is made. The output unit 170 may be a display apparatus such as a display, or a notification apparatus (sound output apparatus) which makes a notification of an alarm or activates the alarm. Further, the output unit 170 may be an external storage apparatus which stores data, a transmission apparatus which transmits data through a communication path, or the like. Further, the output unit 170 may be a communication apparatus in the case where an alert is issued or activated to other apparatuses.

Figure 2:
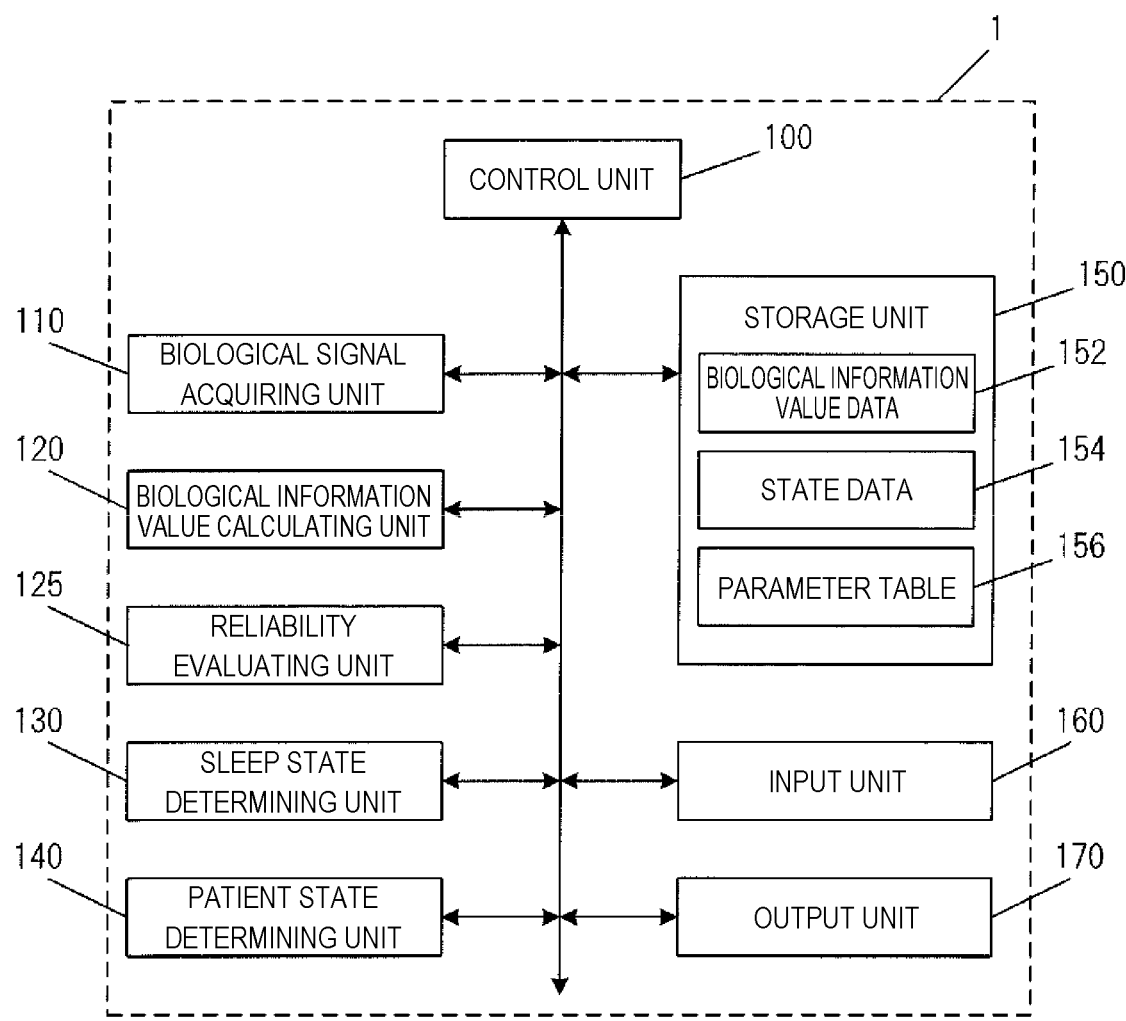
FIG. 2 is a diagram for explaining a configuration of the system in the first embodiment.

Among the above-described components, the biological information value calculating unit 120, the reliability evaluating unit 125, the sleep state determining unit 130 and the patient state determining unit 140 may be implemented by software executed by a microprocessor which constitutes some or all of the components shown in FIG. 2. For example, the control unit 100 reads out and executes software and programs stored in the storage unit 150. If the software is executed, the control unit 100 is implemented as each component.

Further, FIG. 2 schematically explains components of the system 1. These components may be implemented by, for example, one apparatus which can detect vibration or, as illustrated in FIG. 1, may be separately configured as the detection apparatus 3 and the processing apparatus 5. Further, in place of the processing apparatus 5, the processing apparatus 5 may be implemented by an external server which can provide the same service.

Figure 6:
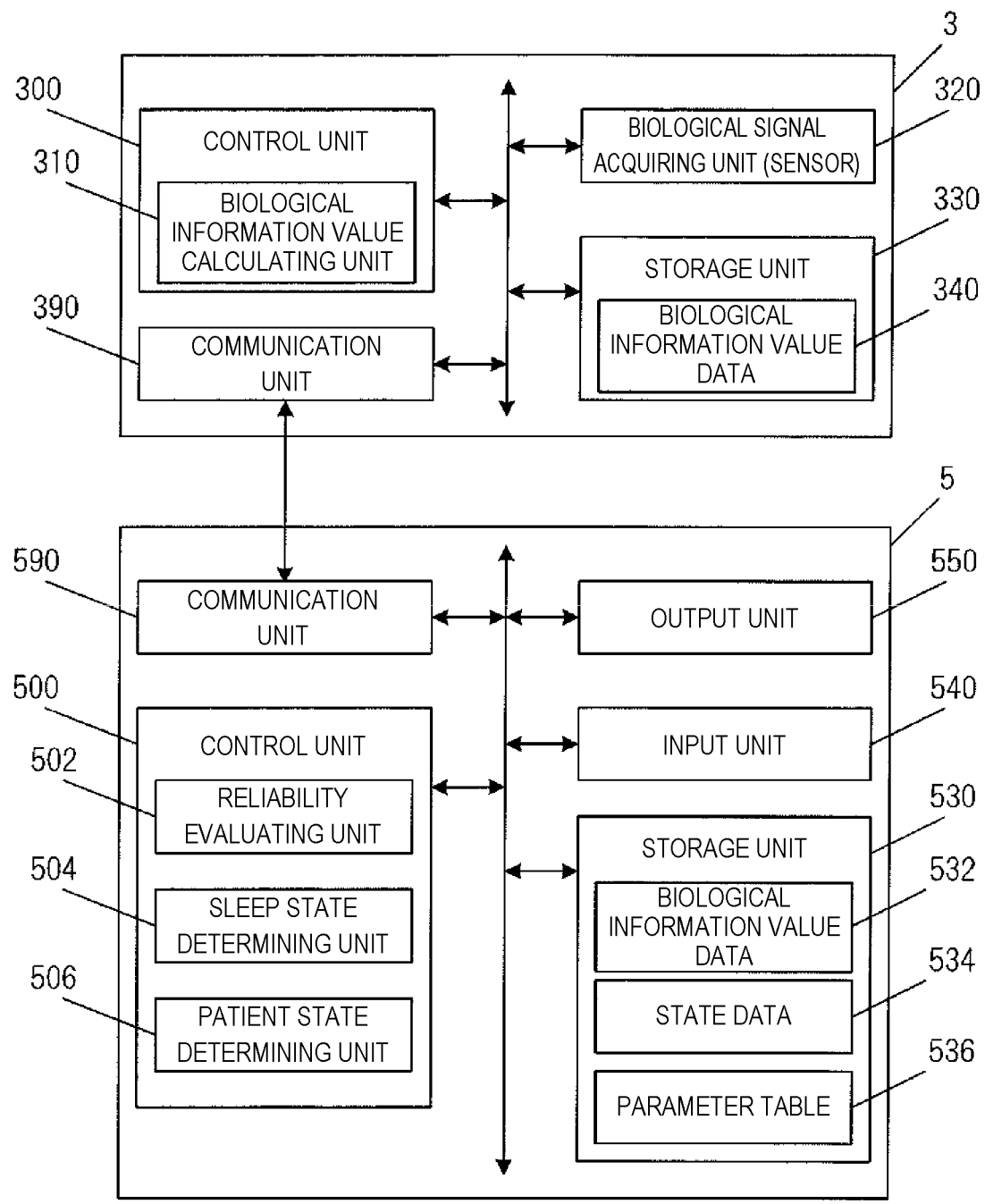
FIG. 6 is a diagram for explaining a configuration of the system in the first embodiment.

A case where the system 1 in FIG. 2 is implemented by the detection apparatus 3 and the processing apparatus 5 in FIG. 1 will be described with reference to FIG. 6. The detection apparatus 3 includes the control unit 300, the biological signal acquiring unit 320 which is a sensor, the storage unit 330 and the communication unit 390.

Further, the control unit 300 functions as the biological information value calculating unit 310 by executing the software (programs) stored in the storage unit 330. The biological information value calculating unit 310 calculates the biological information value on the basis of the biological signal acquired at the biological signal acquiring unit 320. Then, the calculated biological information value is stored in biological information value data 340 or transmitted to the processing apparatus 5 via the communication unit 390. Further, the biological signal acquired at the biological signal acquiring unit 320 can be transmitted to the processing apparatus 5 via the communication unit 390 together with the biological information value.

A timing at which the biological information value (biological information) is transmitted from the detection apparatus 3 to the processing apparatus 5 or a timing at which the biological information value (biological information) is stored in the biological information value data 340 may be real time or for each predetermined time period.

Note that the biological signal acquiring unit 320 is the biological signal acquiring unit 110 in FIG. 2, and the biological information value calculating unit 310 is the biological information value calculating unit 120 in FIG. 2. Further, the communication unit 390 is, for example, a communication interface which can be connected to a network (for example, a LAN/a WAN).

The processing apparatus 5 includes a control unit 500, a storage unit 530, an input unit 540, an output unit 550 and a communication unit 590. The processing apparatus 5 receives the biological information value and the biological signal from the detection apparatus 3 via the communication unit 590. The received biological information value is stored in biological information value data 532.

The control unit 500 functions as a reliability evaluating unit 502, a sleep state determining unit 504 or a patient state determining unit 506 by executing software (programs) stored in the storage unit 530. On the basis of the received biological information value and biological signal, the reliability evaluating unit 502 determines reliability of the biological information value, the sleep state determining unit 504 determines a state of the patient related to whether the patient is sleeping or waking, and the patient state determining unit 506 determines the state of the patient.

Note that the reliability evaluating unit 502 is the reliability evaluating unit 125 in FIG. 2. The sleep state determining unit 504 is the sleep state determining unit 130 in FIG. 2. The patient state determining unit 506 is the patient state determining unit 140 in FIG. 2. The input unit 540 is the input unit 160 in FIG. 2. The output unit 550 is the output unit 170 in FIG. 2. The storage unit 530 is the storage unit 150 in FIG. 2.

Therefore, the biological information value data 532 stored in the storage unit 530 is the same as the biological information value data 152 in FIG. 2, a state data 534 is the same as the state data 154 in FIG. 2, and a parameter table 536 is the same as the parameter table 156.

[1.3. Processing Flow]
[1.3.1. Heart Rate Calculation Processing]

Figure 7:
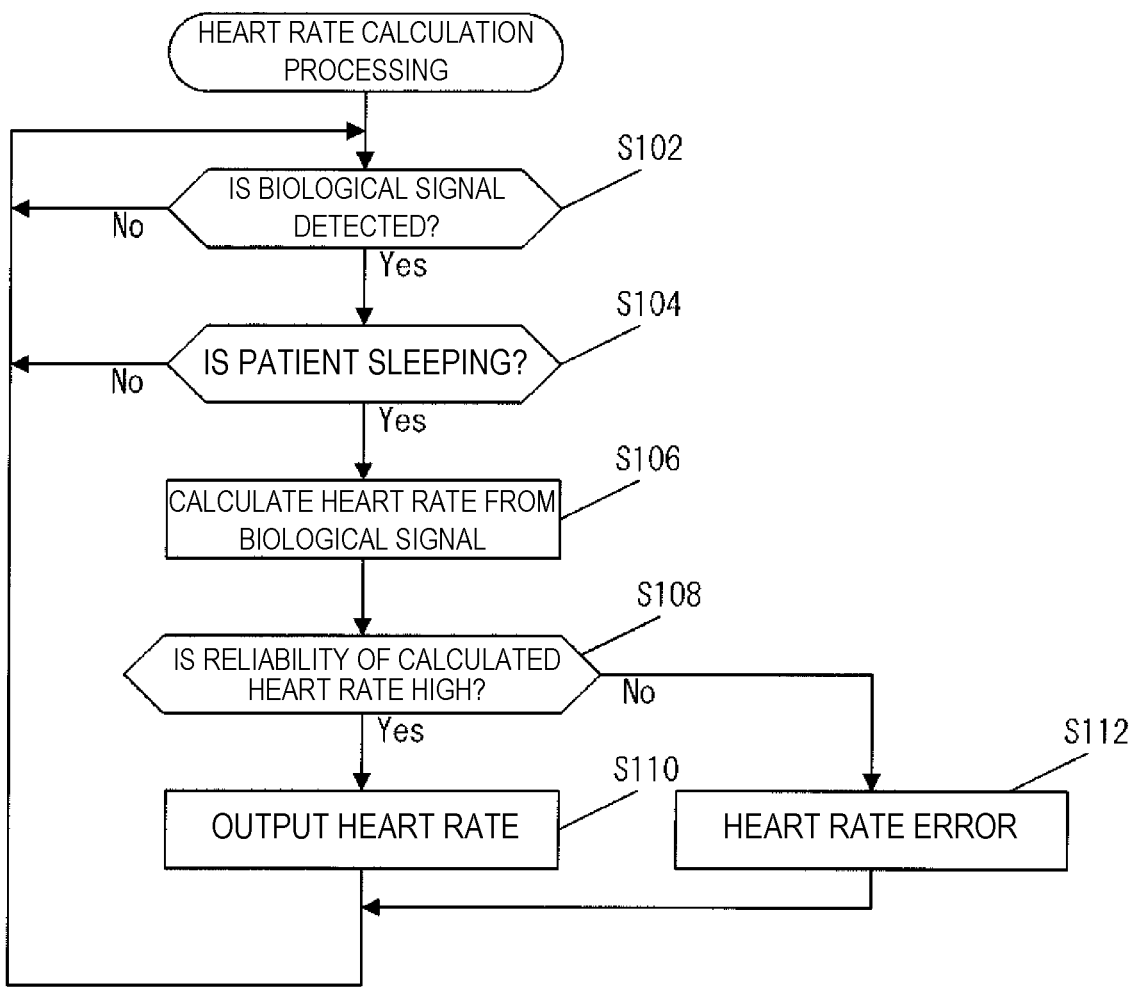
FIG. 7 is an operation flow for explaining heart rate calculation processing in the first embodiment.

Processing the biological information value calculating unit 120 calculates a heart rate as the biological information value will be described with reference to the algorithm or processing flow shown in FIG. 7.

The biological information value calculating unit 120 calculates the biological information value. Specifically, the biological information value calculating unit 120 calculates a heart rate from a biological signal if the biological signal is detected by the biological signal acquiring unit 110 and the patient satisfies heart rate calculation conditions (step S102: Yes→step S104: Yes→step S106). The heart rate calculation conditions described here are used to evaluate the reliability of the biological signal using calculation conditions. One example of the heart rate calculation conditions is whether the sensor correctly detects a signal of the heart rate, or the like.

Here, in step S102, the biological information value calculating unit 120 determines whether the biological signal is detected by the biological signal acquiring unit 110. A case where the biological signal is detected indicates that the patient is staying in bed. Further, in step S104, the control unit 100 (biological information value calculating unit 120) determines whether or not the patient satisfies the heart rate calculation conditions. For example, if the patient is lying on the bed, there is no input of vibration or noise from outside except for vibration of the patient himself or herself, and the patient is lying on the bed in a resting state or at rest (the amount of activity is "0"), or if the sleep state determining unit 130 determines that the patient is sleeping as the state of the patient, the heart rate is calculated (step S104: Yes→step S106).

In step S106, while there are various methods for calculating a heart rate, for example, body motion data is filtered, a heartbeat component is extracted from the body motion data, and an R-R interval is estimated from each heartbeat. Then, the heart rate is calculated on the basis of the R-R interval.

As other methods, it is also possible to calculate a heart rate using a method in which periodicity of body motion data is analyzed and a heart rate is calculated from a peak frequency of body motion data.

Further, in the present embodiment, a value calculated on the basis of the body motion data for each of 30 seconds as a predetermined time period is utilized. Specifically, the heart rate is calculated for each of 30 seconds on the basis of an R-R interval estimated within a time window of 30 seconds and a peak frequency of the body motion data within a time window of 30 seconds.

Subsequently, the reliability evaluating unit 125 determines whether or not reliability of the calculated heart rate is relatively high (step S108). In order to determine whether or not the reliability of the calculated heart rate is relatively high, the method used in the above description of the reliability evaluating unit 125 or a reliability evaluation method disclosed in Japanese Patent Laid-Open No. 2017-47211 (filing date: Sep. 1, 2016, the title of the invention:

BIOLOGICAL INFORMATION OUTPUT DEVICE, BIOLOGICAL INFORMATION OUTPUT METHOD, AND PROGRAM) is used.

Here, if the reliability evaluating unit 125 determines that the reliability of the calculated heart rate is relatively high, the biological information value calculating unit 120 outputs the heart rate as is (step S108: Yes→step S110). On the other hand, if the reliability evaluating unit 125 determines the reliability of the calculated heart rate is relatively low, the heart rate is not output (step S108: No→step S112). Specifically, the biological information value calculating unit 120 may output an error as the heart rate or does not have to output anything. The biological information value calculating unit 120 stores the heart rate in the biological information value data 152.

[1.3.2. Patient State Determination Processing]

Subsequently, patient state determination processing will be described with reference to FIG. 8. First, the patient state determining unit 140 determines whether or not biological value information corresponding to a time period (that is, corresponding to the calculated ratio calculation time period) required for determining the state of the patient is stored in the biological information value data 152.

The calculated ratio calculation time period is stored in the parameter table 156. Here, the calculated ratio calculation time period only has to be equal to or longer than a predetermined time period. The calculated ratio calculation time period is preferably from 30 minutes to 10 hours, and, more preferably, from 4 hours to 8 hours which correspond to a period which the patient is usually sleeping.

Therefore, the calculated ratio calculation time period may be designated as one night (from 11:00 p.m. to 6:00 a.m.), a lights-out time period (from 9:00 p.m. to 6:00 a.m.) or a time period when the patient is staying in the bed (from time at which the patient goes to bed to time at which the patient wakes up). Further, the calculated ratio calculation time period may be designated as a plurality of days such as two days and three days, or days obtained by adding up only days in which the time period when the patient is staying in the bed or the period which the patient is sleeping so as to exceed five hours among a plurality of days.

Subsequently, if the patient state determining unit 140 determines biological value information corresponding to a time period required for determining the state of the patient is stored in the biological information value data 152 (step S152 Yes), the patient state determining unit 140 determines a calculated heart rate ratio (step S154). In this calculation, a calculated heart rate ratio indicates a ratio of a time period in which a heart rate is calculated with high reliability to the above-described calculated ratio calculation time period. The ratio of a time period in which a heart rate is calculated with high reliability to the above-described calculated ratio calculation time period is calculated as the calculated heart rate ratio. The patient state determining unit 140 then determines whether or not the calculated heart rate ratio is equal to or less than a threshold of calculated heart rate ratio (step S156). The threshold of calculated heart rate ratio is stored in the parameter table 156, and is "80%" on the basis of FIG. 5.

Therefore, the patient state determining unit 140 determines that there is an abnormality in heartbeat (for example, the patient has tendency of arrhythmia or atrial fibrillation, or there is an abnormality in a cardiopulmonary function) if the calculated heart rate ratio is equal to or less than "80%" and outputs an abnormality of the heartbeat (step S158).

Note that, while the calculated heart rate ratio is determined in FIG. 8, a ratio of the heart rate not being calculated with high reliability, that is, the uncalculated heart rate ratio may be utilized instead of the calculated heart rate ratio.

The patient state determining unit 140 calculates a ratio of a time period in which a heart rate is not correctly calculated to the calculated ratio calculation time period as the uncalculated heart rate ratio. The patient state determining unit 140 then determines whether or not the uncalculated heart rate ratio is greater (equal to or greater) than the threshold of uncalculated heart rate ratio. The uncalculated heart rate ratio is stored in the parameter table 156 and is "20%" on the basis of FIG. 5.

Therefore, the patient state determining unit 140 determines that there is an abnormality in the heartbeat if the uncalculated heart rate ratio exceeds "20%", and outputs an abnormality of the heartbeat.

[1.4. Example]

Figure 9A:
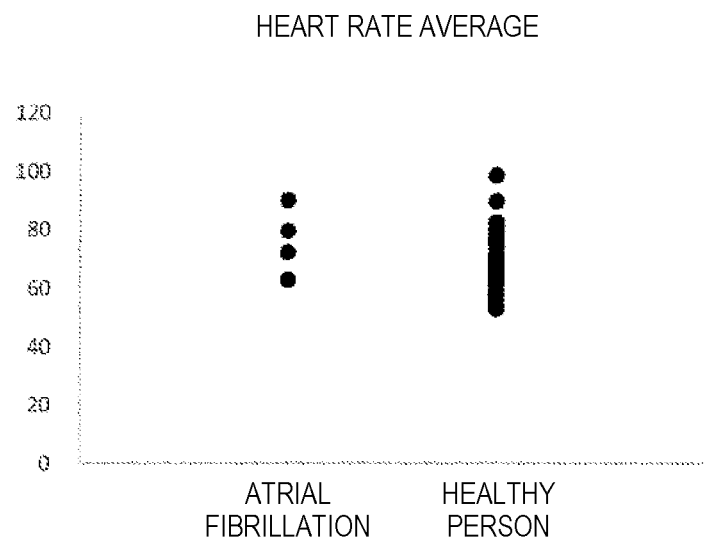
FIGS. 9A-9C are diagrams for explaining examples in the first embodiment.
Figure 9B:
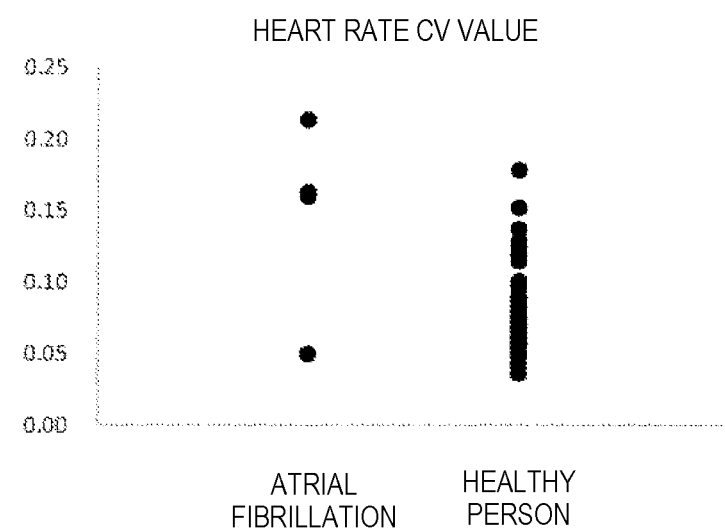
Figure 9C:
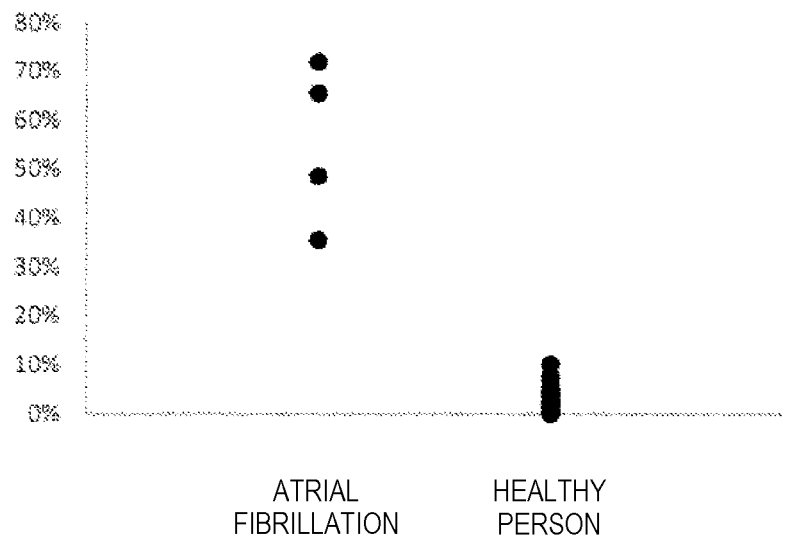

An example in the present embodiment will be described with reference to FIG. 9A to 9C. FIG. 9A to 9C are comparative graphs of between a person who has an abnormality in heartbeat (a person for whom atrial fibrillation is detected) and a healthy person. The comparative graphs are generated using a heart rate which is calculated every 30 seconds, and, in all the graphs, a left side of each comparative graph indicates a patient who suffers from atrial fibrillation and a right side of each comparative graph indicates a healthy person.

FIG. 9A is a diagram illustrating an average of the heart rate, and FIG. 9B is a diagram illustrating a variation coefficient (CV value) of the heart rate. As can be seen from these graphs, it is impossible to correctly discern between a patient and a healthy person only with the conventional indexes.

FIG. 9C is a diagram illustrating the uncalculated heart rate ratio. Distribution of the patient who suffers from atrial fibrillation and the healthy person is divided around the uncalculated ratio of approximately "20%".

Therefore, by utilizing the uncalculated heart rate ratio (calculated heart rate ratio), it is possible to appropriately determine the state of the patient and an abnormality of the biological information. Further, if it is determined that there is an abnormality, it is possible to output the information.

[2. Second Embodiment]

Figure 10:
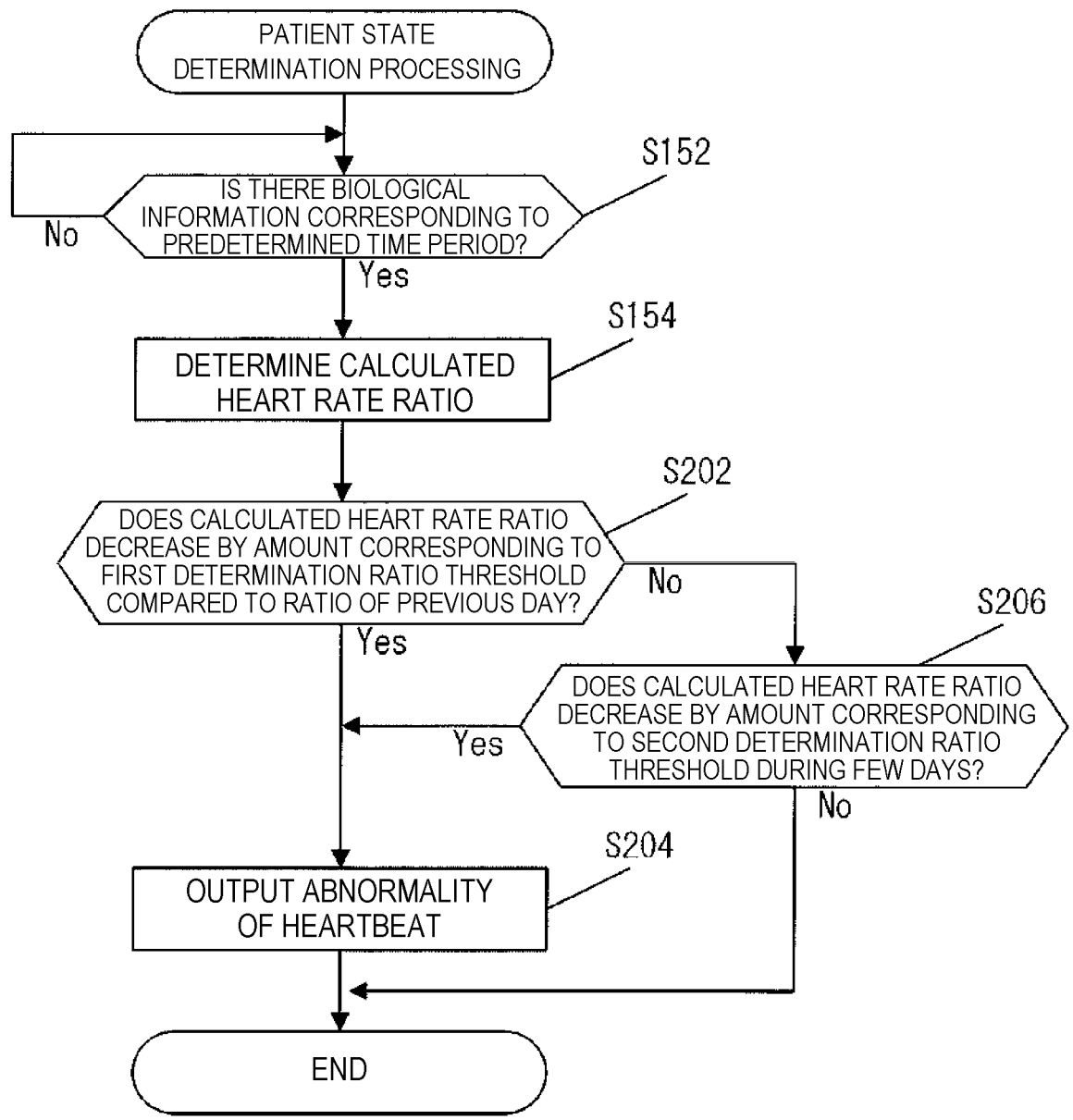
FIG. 10 is an operation flow for explaining patient state determination processing in a second embodiment.

A second embodiment will be described in FIG. 10. The second embodiment is substantially the same as the first embodiment in a configuration, processing, or the like. The second embodiment differs from the first embodiment in that the patient state determination processing in FIG. 8 is replaced with patient state determination processing in FIG. 10.

The second embodiment will be described below mainly with reference to the algorithm or processing flow shown in FIG. 10. Note that the same reference numerals will be assigned to processing which is the same as that in the first embodiment, and detailed description will be omitted.

After the patient state determining unit 140 determines the calculated heart rate ratio (step S154), the patient state determining unit 140 outputs an abnormality in heartbeat if the calculated heart rate ratio decreases by an amount corresponding to a first determination ratio threshold compared to the ratio of the previous day (step S202: Yes→step S204). In the present embodiment, the patient state determining unit 140 determines the state of the patient by comparing the calculated heart rate ratio with the calculated heart rate ratio of the previous day in addition to performing comparison within one day. Note that the first determination ratio threshold may be stored in the parameter table 156, and is preferably from 5% to 30%. For example, if the calculated heart rate ratio precipitously decreases, the patient state determining unit 140 determines that there is some kind of abnormality, and makes a notification or activates an alarm.

Further, while the calculated heart rate ratio is within the first determination ratio threshold in comparison with the previous day, if the patient state determining unit 140 determines that the calculated heart rate ratio decreases by an amount corresponding to a second determination ratio threshold during a few days, the patient state determining unit 140 determines that there is some kind of abnormality, and an abnormality of heartbeat is output (step S202: No→step S206: Yes→step S204).

Note that the second determination ratio threshold may be stored in the parameter table 156, and is preferably from 10% to 20%.

In this manner, according to the present embodiment, by determining fluctuation of the calculated heart rate ratio from the previous day or during a few days, the patient state determining unit 140 determines the state of the patient more appropriately.

[3. Effects]

In this manner, according to the present embodiment, by utilizing a non-wearable type body motion (vibration) sensor, it becomes possible to appropriately determine an abnormality of biological information such as arrhythmia. If an abnormality of biological information is determined by utilizing conventional electrocardiogram, it is necessary to directly attach electrodes to the patient. Therefore, there is great burden on the patient.

However, in the present embodiment, it is only necessary to place the apparatus between the mattress and the sections of the bed, for example, when the patient goes to bed, and it becomes possible to determine an abnormality of biological information using a method which places less burden on the patient.

In particular, since an occurrence frequency of arrhythmia is not obvious, it takes a large amount of time to find arrhythmia through examination. In the present embodiment, it becomes also easy to perform measurement for a long period of time using a method which places less burden on the patient. Further, by performing measurement for a long period of time, it becomes not only possible to shorten time to find arrhythmia, but also possible to reduce errors and improve determination accuracy.

[4. Modified Examples]

While the embodiments have been described in detail above with reference to the drawings, the specific configuration is not limited to the embodiments, and design, or the like, which are within the scope not deviating from the gist of the present invention are included in the claims.

Further, while, in the present embodiment, the biological information is output from the processing apparatus 5 on the basis of the result output from the detection apparatus 3, the detection apparatus 3 may perform all calculation. Further, as well as a configuration where application is installed and implemented at a terminal apparatus (for example, a smartphone, a tablet and a computer), it is, for example, also possible to perform processing on the server side and return the processing result to the terminal apparatus.

For example, the above-described processing may be executed on the server side by the biological information being uploaded to the server from the detection apparatus 3. The detection apparatus 3 may be implemented by an apparatus such as a smartphone in which, for example, an acceleration sensor and a vibration sensor are incorporated.

Further, a program running at each apparatus in the present embodiment is a program of controlling a CPU, or the like, (a program for causing a computer to function) to execute the functions of the above-described embodiments. Information handled at these apparatuses is temporarily accumulated in a temporal storage apparatus (for example, a RAM) upon the processing, and, then, stored in a storage apparatus such as various kinds of ROMs, HDDs and SSDs, and read out, corrected and written by the CPU as necessary.

Further, in the case where the program is distributed to the market, it is possible to distribute the program stored in a portable recording medium, or forward the program to a server computer connected via a network such as the Internet. In this case, the storage apparatus of the server computer is, of course, also included in the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus comprising:
   a sensor placed between a bottom frame of a bed and a mattress, the sensor configured to acquire biological signals of a user; and
   a controller configured:
      to calculate a first period of time as a period of time for which a first metric is obtained from the biological signals when the user is in a lying state on the mattress, and
      to activate an alarm indicating a heart abnormality status of the biological signals of the user, if a first ratio of the first period of time to a set period of time is less than a first threshold.

2. The apparatus according to claim 1, wherein the biological signals are heart rate signals.

3. The apparatus according to claim 1, wherein the controller is configured to determine whether or not the user is lying down on the mattress and the controller only calculates biological information of the user based on the biological signals if the user is determined to be lying down on the mattress, and the controller is configured to store the biological signals during the first period of time and not to store the biological signals during a second period of time when the user is not in a lying state on the mattress, wherein the biolgicial signals are heart rate signals.

4. The apparatus according to claim 1, wherein the controller determines whether or not the user is sleeping and calculates the first ratio only if the user is determined to be sleeping.

5. The apparatus according to claim 1, wherein the biological signals are heart rate signals, wherein the controller is configured to record the first ratio on a first day, to subsequently record the first ratio on the following day, and to also record the first ratio during a plurality of days, wherein the controller is configured to activate an alarm, if the first ratio recorded on the following day decreases by a first amount compared to the first ratio recorded on the first day, wherein the controller is configured to activate an alarm, if the first ratio of the following day does not decrease by the first amount compared to the first ratio of the first day and the first ratio of the following day decreases by a second amount compared to the first ratio recorded during the plurality of days, and wherein the controller is configured not to activate an alarm, if the first ratio of the following day does not decrease by the first amount compared to the first ratio of the first day and the first ratio of the following day does not decrease by the second amount compared to the first ratio recorded during the plurality of days, the first amount being different from the second amount.

6. The apparatus according to claim 5, wherein
the first amount is selected from 5% to 30% and the second amount is selected from 10% to 20%.

7. The apparatus according to claim 1, wherein
the biological signals are related to heartbeats, and the controller is configured to activate the alarm to indicate that the user has an atrial fibrillation if the first ratio is less than the first threshold.

8. A method comprising:
acquiring, with a sensor, biological signals of a user, the sensor placed between a bottom frame of a bed and a mattress;
calculating, with a controller, first period of time as a period of time for which a first metric is obtained from the biological signals when the user is in a lying state on the mattress; and
activating, with a controller, an alarm indicating a heart abnormality status of the biological signals of the user, if a first ratio of the first period of time to a set period of time is less than a first threshold.

9. The method according to claim 8, wherein the biological signals are heart rate signals.

10. The method according to claim 8, further comprising:
determining, with the controller, whether or not the user is lying down on the mattress;
calculating, with the controller, biological information of the user based on the biological signals only if the user is determined to be lying down on the mattress; and
storing, with the controller, the biological signals during the first period of time and not storing, with the controller, the biological signals during a second period of time when the user is not in a lying state on the mattress,
wherein the biologicial signals are heart rate signals.

11. The method according to claim 8, further comprising:
determining, with the controller, whether or not the user is sleeping and calculates the first ratio only if the user is determined to be sleeping.

12. The method according to claim 8,
wherein the biological signals are heart rate signals,
wherein the controller is configured to record the first ratio on a first day, to subsequently record the first ratio on the following day, and to also record the first ratio during a plurality of days,
wherein the controller is configured to activate an alarm, if the first ratio recorded on the following day decreases by a first amount compared to the first ratio recorded on the first day,
wherein the controller is configured to activate an alarm, if the first ratio of the following day does not decrease by the first amount compared to the first ratio of the first day and the first ratio of the following day decreases by a second amount compared to the first ratio recorded during the plurality of days, and
wherein the controller is configured not to activate an alarm, if the first ratio of the following day does not decrease by the first amount compared to the first ratio of the first day and the first ratio of the following day does not decrease by the second amount compared to the first ratio recorded during the plurality of days, the first amount being different from the second amount.

13. The method according to claim 12, further comprising:
selecting, with the controller, the first amount from 5% to 30% and selecting, with the controller, the second amount from 10% to 20%.

14. The method according to claim 8, wherein
the biological signals are related to heartbeats, and the activating, with the controller, activates the alarm to indicate that the user has an atrial fibrillation if the first ratio is less than the first threshold.

15. A non-transitory computer readable medium having stored thereon a program for causing a computer to execute at least the following:
acquiring, with a sensor, biological signals of a user, the sensor placed between a bottom frame of a bed and a mattress;
calculating a first period of time as a period of time for which a first metric is obtained from the biological signals when the user is in a lying state on the mattress; and
activating an alarm indicating a heart abnormality status of the biological signals of the user, if a first ratio of the first period of time to a set period of time is less than a first threshold.

16. The non-transitory computer readable medium according to claim 15,
wherein the biological signals are heart rate signals.

17. The non-transitory computer readable medium according to claim 15, the program further causing a computer to execute at least the following:
determining whether or not the user is lying down on the mattress;
calculating biological information of the user based on the biological signals only if the user is determined to be lying down on the mattress; and
storing the biological signals during the first period of time and not storing the biological signals during a second period of time when the user is not in a lying state on the mattress,
wherein the biologicial signals are heart rate signals.

18. The non-transitory computer readable medium according to claim 15, the program further causing a computer to execute at least the following:
determining whether or not the user is sleeping and calculates the first ratio only if the user is determined to be sleeping.

19. The non-transitory computer readable medium according to claim 15, the program further causing a computer to execute at least the following:
record the first ratio on a first day, subsequently record the first ratio on the following day, and also record the first ratio during a plurality of days,
activate an alarm, if the first ratio recorded on the following day decreases by a first amount compared to the first ratio recorded on the first day,
activate an alarm, if the first ratio of the following day does not decrease by the first amount compared to the first ratio of the first day and the first ratio of the following day decreases by a second amount compared to the first ratio recorded during the plurality of days, and not activate an alarm, if the first ratio of the following day does not decrease by the first amount compared to the first ratio of the first day and the first ratio of the following day does not decrease by the second amount compared to the first ratio recorded during the plurality of days, the first amount being different from the second amount, wherein the biological signals are heart rate signals.

20. The non-transitory computer readable medium according to claim 19, the program further causing a computer to execute at least the following:

selecting the first amount from 5% to 30% and selecting the second amount from 10% to 20%.

21. The non-transitory computer readable medium according to claim 15, wherein the biological signals are related to heartbeats, and the activating an alarm activates the alarm to indicate that the user has an atrial fibrillation if the first ratio is less than the first threshold.

* * * * *